(12) United States Patent
Shikata (10) Patent No.: US 7,966,884 B2
(45) Date of Patent: Jun. 28, 2011

(54) TWO-DIMENSIONAL-ARRAY ULTRASONIC PROBE AND ULTRASONIC DIAGNOSTIC SYSTEM

(75) Inventor: Hiroyuki Shikata, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 558 days.

(21) Appl. No.: 12/017,565

(22) Filed: Jan. 22, 2008

(65) Prior Publication Data
US 2008/0173094 A1    Jul. 24, 2008

(30) Foreign Application Priority Data

Jan. 23, 2007 (JP) ................................. 2007-012842

(51) Int. Cl.
*G01N 29/04* (2006.01)
(52) U.S. Cl. .......................................... 73/625; 73/626
(58) Field of Classification Search .................. 73/625, 73/626, 634, 618, 620; 600/459
See application file for complete search history.

(56) References Cited

U.S. PATENT DOCUMENTS

| | | | | |
|---|---|---|---|---|
| 4,434,661 A * | 3/1984 | Miwa et al. | ..................... | 73/625 |
| 5,044,370 A * | 9/1991 | Dubut et al. | .................. | 600/459 |
| 5,327,895 A * | 7/1994 | Hashimoto et al. | ........... | 600/459 |
| 5,569,545 A * | 10/1996 | Yokono et al. | ................. | 428/626 |
| 6,297,467 B1 * | 10/2001 | Maev et al. | ..................... | 219/109 |
| 6,994,674 B2 | 2/2006 | Sheljaskow et al. | | |
| 7,082,679 B2 * | 8/2006 | Myoung et al. | ................. | 29/830 |
| 7,678,054 B2 * | 3/2010 | Okazaki et al. | ................ | 600/459 |
| 2005/0165314 A1 | 7/2005 | Tanaka | .......................... | 600/459 |

FOREIGN PATENT DOCUMENTS

JP    2004-41730    2/2004

* cited by examiner

*Primary Examiner* — Jacques M Saint Surin
(74) *Attorney, Agent, or Firm* — Oblon, Spivak, McClelland, Maier & Neustadt, L.L.P.

(57) ABSTRACT

A two-dimensional array ultrasonic probe has an ultrasonic transducer. The transducer has transducer elements that are arranged in a first direction and a second direction, forming a lattice. Acoustic-emission electrodes are provided on the acoustic-emission surfaces of the transducer elements. Back electrodes are provided on the backs of the transducer elements. A transmitting-circuit unit is connected to the acoustic-emission electrodes. A receiving-circuit unit is connected to the back electrodes. Of the acoustic-emission electrodes, two electrodes are short-circuited to the transmitting circuits of the transmitting-circuit unit. The remaining two acoustic-emission electrodes are short-circuited to the receiving circuits of the receiving-circuit unit.

21 Claims, 10 Drawing Sheets

TWO-DIMENSIONAL-ARRAY ULTRASONIC PROBE AND ULTRASONIC DIAGNOSTIC SYSTEM

CROSS-REFERENCE TO RELATED APPLICATIONS

This application is based upon and claims the benefit of priority from prior Japanese Patent Application No. 2007-012842, filed Jan. 23, 2007, the entire contents of which are incorporated herein by reference.

BACKGROUND OF THE INVENTION

1. Field of the Invention

The present invention relates to an ultrasonic diagnostic apparatus that transmits ultrasonic waves to a patient, receives the waves reflected from the patient and processes the waveforms received, thereby displaying, on a screen, tomograms for use in making a diagnosis. More particularly, this invention relates to a two-dimensional ultrasonic probe to be connected to an ultrasonic diagnostic apparatus that can provide three-dimensional images in real time, and also to an ultrasonic diagnostic system.

2. Description of the Related Art

Any ultrasonic probe comprises a two-dimensional array transducer that has elements arranged in the form of a two-dimensional lattice.

A conventional two-dimensional array transducer comprises a backing material and a plurality of ultrasonic transducer elements. The transducer elements 6 are arranged on the backing material, in the form of a two-dimensional lattice. Two electrodes are provided for each transducer element. One electrode is provided on the acoustic emission surface of the element, and the other electrode is provided on the back of the element, which contacts backing material. These electrodes are connected to transmitting circuits (not shown) and receiving circuits (not shown). Further, an acoustic member, such as an acoustic adjustment layer, an acoustic lens or a bio-contact member, is arranged on the acoustic emission surface of each transducer element.

Figure 1:
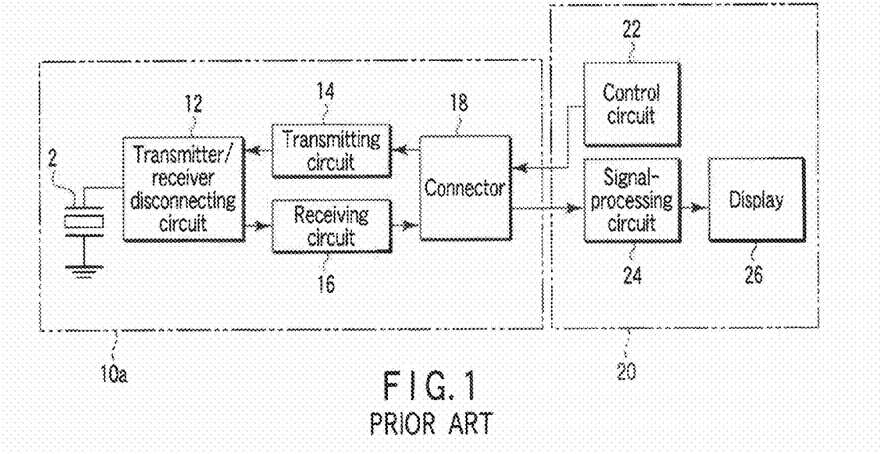
FIG. 1 is a block diagram presenting the configuration of a conventional ultrasonic diagnostic system.

FIG. 1 is a block diagram presenting the configuration of a conventional ultrasonic diagnostic system.

As FIG. 1 shows, the ultrasonic diagnostic system comprises an ultrasonic probe 10a and an ultrasonic diagnostic apparatus 20. The ultrasonic probe 10a has a two-dimensional array transducer 2, a transmitter/receiver disconnecting circuit 12, a transmitting circuit 14, a receiving circuit 16, and a connector 18. The ultrasonic diagnostic apparatus 20 has a control circuit 22, a signal-processing circuit 24, and a display 26.

The two-dimensional array transducer 2 has transducer elements, each connected to a signal line. The signal line is connected to the transmitting circuit (balser) 14 and the receiving circuit (receiver) 16, both provided in the ultrasonic probe la or in the ultrasonic diagnostic apparatus 20. (In the case shown in FIG. 1, the transmitting circuit 14 and the receiving circuit 16 are provided in the ultrasonic probe 10a.) In the ultrasonic diagnostic apparatus 20, the signal-processing circuit 24 performs analog-to-digital conversion on the signal that the receiver 16 has received, so that a tomogram may be displayed on the display 26 (e.g., CRT monitor) after an envelope, for example, has been detected. Further, since the two-dimensional array transducer can transmit and receive ultrasonic waves coming in any directions in space, the signal can be converted to data representing a tomogram of any desired region or can be subjected to three-dimensional rendering. Hence, the display 26 can display a tomogram or a three-dimensional image in real time.

In the conventional one-dimensional array transducer, the strip-shaped transducer elements are linearly arranged. About 100 elements are so arranged in most cases. By contrast, in any two-dimensional array transducer, thousands of transducer elements are arranged in rows and columns, and the probe cable is thick if it contains the signal lines of all transducer elements. The thicker the probe cable, the lower the operability of the ultrasonic probe having the two-dimensional array transducer. In view of this, most ultrasonic probes incorporate transmitting circuits and receiving circuits.

Two electrodes are provided, respectively, on the acoustic emission surface and back of each element of a two-dimensional array transducer. In most two-dimensional array transducers, the electrodes provided on the acoustic emission surfaces are bundled together and connected to the transmitting circuit and receiving circuit through a transmitter/receiver disconnecting circuit, whereas the electrodes provided on the backs are connected, independently of one another, to the transmitting circuit and receiving circuit through the transmitter/receiver disconnecting circuit. In this case, the voltage of the pulses transmitted is generally 100V or more. This voltage raises breakdown problems in most ICs manufactured by the ordinary process of producing low-breakdown-voltage devices.

Therefore, the transmitter/receiver disconnecting circuit is constituted by an IC manufactured by a special process of producing high breakdown-voltage devices. The transmitter/receiver disconnecting circuit is inevitably not only expensive, but is also large and consumes much power. If incorporated into a probe, the probe will be large and have low operability. Further, the transmission voltage must be reduced to keep the probe temperature below a prescribed value, thereby ensuring safety. If the transmission voltage is so reduced, the sensitivity of the probe will decrease. Consequently, the probe will raise problems in terms of image quality.

Figure 2:
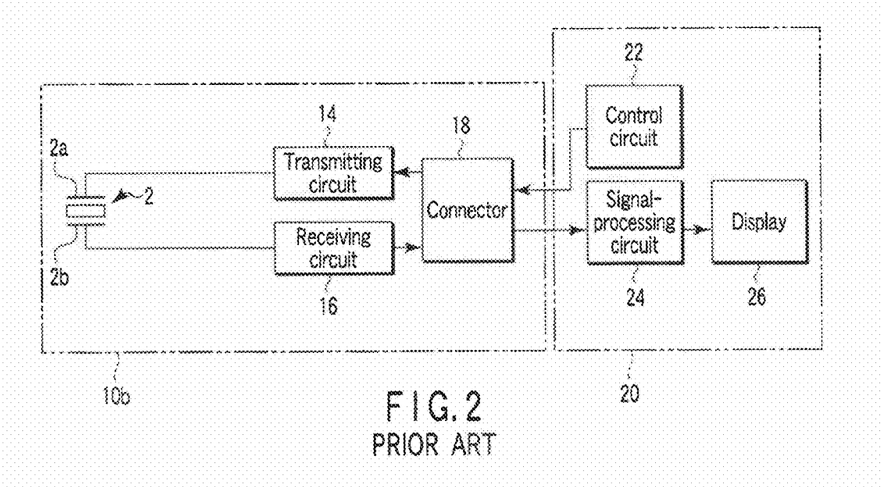
FIG. 2 is a block diagram presenting a conventional ultrasonic diagnostic system of a different configuration.

In view of the above, the transmitting circuit 14 and the receiving circuit 16 may be connected, respectively, to the electrodes 2a provided on the acoustic emission surface of the transducer 2 and be connected to the electrodes 2a provided on the back of the transducer 2, as is shown in FIG. 2. In this case, the receiving circuit 16 is held short-circuited while the transmitting circuit 14 is transmitting a signal, and transmitting circuit 14 is held AC short-circuited, while the receiving circuit 16 is receiving a signal. The transmitting circuit 14 and the receiving circuit 16 are thus disconnected from each other. Such an ultrasonic probe as shown in FIG. 2 is disclosed in, for example, Jpn. Pat. Appln. KOKAI Publication No. 2004-41730. In this technique, the transducer can, by itself, disconnect the transmitting circuit and the receiving circuit from each other. A transmitter/receiver disconnecting circuit need not be used at all. The receiving circuit can be an inexpensive IC manufactured by the ordinary process of producing low breakdown-voltage devices. In addition, since no transmitter/receiver disconnecting circuit is required, the ultrasonic probe can be smaller and consumes less power.

Even if the technique disclosed in the Jpn. Pat. Appln. KOKAI Publication No. 2004-41730 is employed, however, transmitting circuits and receiving circuits must be provided in the same numbers as the transducer elements. In order to prevent an increase in the size of the circuitry provided in the probe, the total number of elements should be smaller than a certain value.

Generally, it is necessary to raise the frequency or increase the aperture in order to attain a high resolution. If the frequency is raised or the aperture is increased, while using a limited number of transducer elements, however, the product of the frequency and the pitch of elements will inevitably increase. Consequently, the grating lobe, i.e., transmission or reception in a direction other than the intended direction, become prominent. Hence, the frequency cannot be raised or the aperture cannot be increased in order to attain a high resolution.

In order to attain a large aperture, transmitting circuits and receiving circuits may be used in smaller numbers and a limited number of channels may be connected to these transmitting and receiving circuits. This technique (known as sparse arraying) decreases the ratio of the effective transmission-reception area to the aperture area, reducing the sensitivity of the probe or generates side lobes in the same way as grating lobes are generated. The side lobes decrease the resolution, because they extend in various directions.

BRIEF SUMMARY OF THE INVENTION

Accordingly, an object of the present invention is to provide a two-dimensional array ultrasonic probe that has as small a transmitting-circuit section and a receiving-circuit section as possible and yet has a large aperture and high sensitivity, not influenced by grating lobes, and to provide an ultrasonic diagnostic system that has such a two-dimensional array ultrasonic probe.

An ultrasonic probe according to the present invention comprises: a plurality of ultrasonic transducer elements, each of which has a first electrode and a second electrode provided on an acoustic-emission surface and a back, respectively; transmitting circuits each of which is connected to one of the first and second electrodes; and receiving circuits each of which is connected to the other of the first and second electrodes. At least two of ultrasonic transducer elements are short-circuited to at least one of the first and second electrodes, and the first and second electrodes achieves short-circuiting in different patterns.

An ultrasonic diagnostic system according to the present invention has an ultrasonic probe designed to apply and receive ultrasonic waves to and from a subject, thereby to acquire information about tissues existing in the subject. The ultrasonic probe comprises a plurality of ultrasonic transducer elements, each of which has a first electrode and a second electrode provided on an acoustic-emission surface and a back, respectively, transmitting circuits each of which is connected to one of the first and second electrodes, and receiving circuits each of which is connected to the other of the first and second electrodes. The first and second electrodes are short-circuited to different ultrasonic transducer elements, respectively.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described, with reference to the accompanying drawings.

First Embodiment

Figure 3:
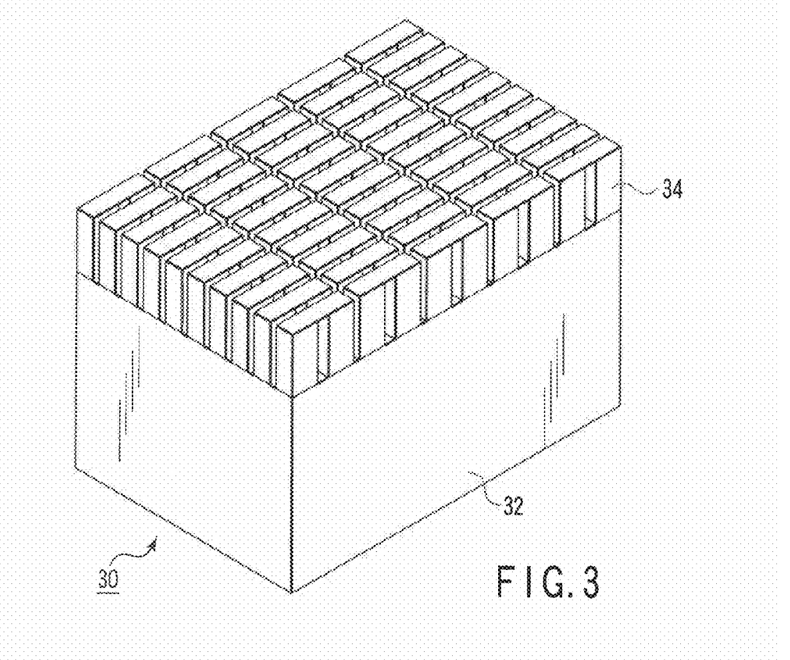
FIG. 3 is a perspective view representing the configuration of the transducer unit of a two-dimensional array ultrasonic probe according to a first embodiment of the present invention.

FIG. 3 is a perspective view representing the configuration of the transducer unit of a two-dimensional array ultrasonic probe according to the first embodiment of the present invention.

As shown in FIG. 3, the transducer unit 30 of the two-dimensional array ultrasonic probe comprises a backing material 32 and a plurality of ultrasonic transducer elements 34. The transducer elements 34 are arranged on the backing material 32, in the form of a two-dimensional lattice. Electrodes are provided on the acoustic emission surfaces of the elements 34, and other electrodes are provided on the backs of the elements 34, which contact backing material 32. These electrodes are connected to transmitting circuits (not shown) and receiving circuits (not shown). Further, an acoustic member, such as an acoustic adjustment layer, an acoustic lens or a bio-contact member, is arranged on the acoustic emission surface of each transducer element 34.

Figure 4:
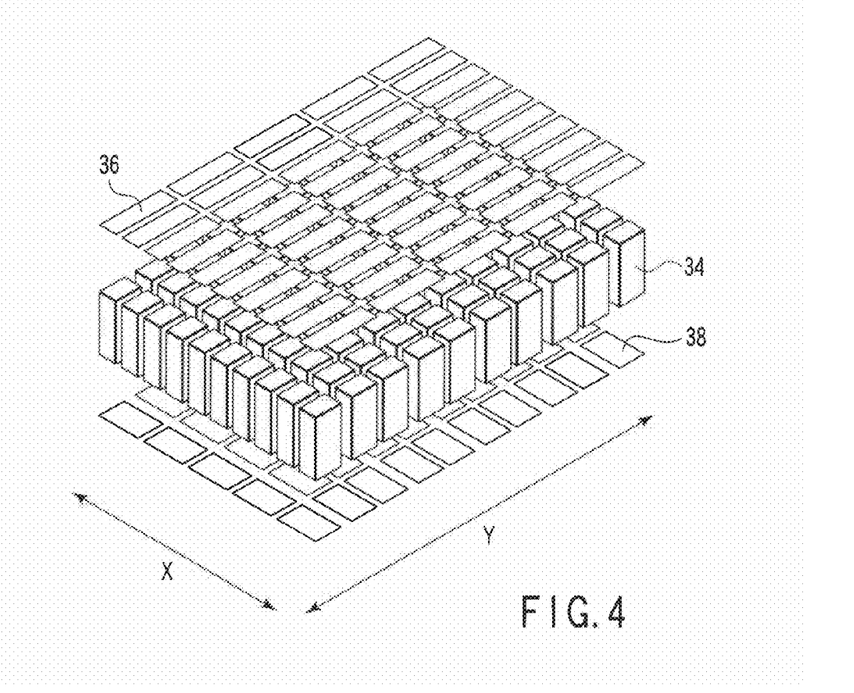
FIG. 4 is a perspective view showing a pattern in which the electrodes of the transducer unit are arranged in the first embodiment of the invention.

FIG. 4 is a perspective view showing a pattern in which the electrodes are arranged with respect to the ultrasonic transducer elements 34 in the first embodiment of the invention. In FIG. 4, the ultrasonic transducer elements (hereinafter referred to as piezoelectric elements) 34 are shown as if separated from the electrodes 36 provided on the acoustic emission surfaces and from the electrodes 38 provided on the backs. In this embodiment, any two adjacent piezoelectric elements 34 arranged in a first direction are short-circuited by one electrode 36 provided on their acoustic emission surfaces, and any two adjacent piezoelectric elements 34 arranged in a second direction intersecting at right angles with the first direction are short-circuited by one electrode 38 provided on their backs.

Transmitting circuits (not shown) are connected to the acoustic-emission electrodes 36 and receiving circuits are connected to the back electrodes, by a signal-line board, such as a flexible printed-circuit (FPC) board (not shown in FIG. 4). As a result, the two-dimensional array ultrasonic transducer unit 30 has such a circuit configuration as shown in FIG. 5.

Figure 5:
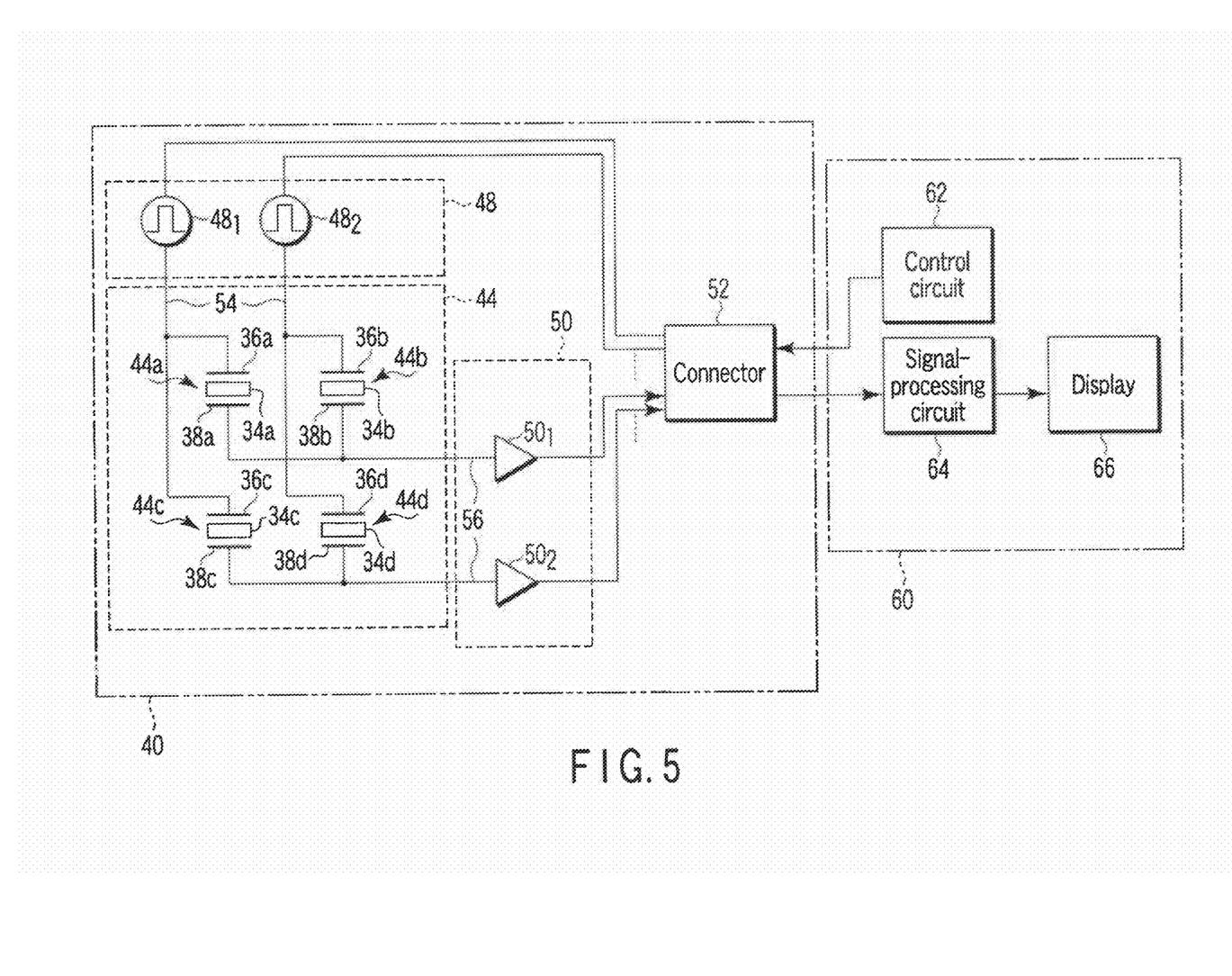
FIG. 5 is a diagram showing the configuration of an ultrasonic diagnostic system including the ultrasonic probe according to the first embodiment of the invention.

FIG. 5 is a diagram showing the configuration of an ultrasonic diagnostic system that includes an ultrasonic probe according to a first embodiment of the present invention.

FIG. 5 shows only four ultrasonic transducer elements 44a to 44d. The transducer element 44a comprises a piezoelectric element 34a, an acoustic-emission electrode 36a, and a back electrode 38a. The transducer element 44b comprises a piezoelectric element 34b, an acoustic-emission electrode 36b, and a back electrode 38b. The transducer element 44c comprises a piezoelectric element 34c, an acoustic-emission electrode 36c, and a back electrode 38c. The transducer element 44d comprises a piezoelectric element 34d, an acoustic-emission electrode 36d, and a back electrode 38d. Two transmitting circuits $48_1$ and $48_2$ provided in a transmitting-circuit unit 48 are connected by an FPC board 54. Similarly, two receiving circuits $50_1$ and $50_2$ provided in a receiving-circuit unit 50 are connected by an FPC board 56. The FPC board 54 and the FPC board 56, which are flexible printed circuit boards, are composed of a base made of polyimide film and a conductor pattern made of copper foil and formed on the base. The two ultrasonic transducer elements connected to which one transmitting circuit is connected differ from the two ultrasonic transducer elements to which one receiving circuit is connected.

For example, the transmitting circuit $48_1$ is connected by the FPC board 54 to the acoustic-emission electrode 36a of the transducer element 44a and the acoustic-emission electrode 36c of the transducer element 44c, and the transmitting circuit $48_2$ is connected by the FPC board 54 to the acoustic-emission electrode 36b of the transducer element 44b and the acoustic-emission electrode 36d of the transducer element 44d. The receiving circuits $50_1$ is connected by the FPC 56 to the back electrode 38a of the transducer element 44a and the back electrode 38b of the transducer element 44b, and receiving circuits $50_2$ is connected by the FPC 56 to the back electrode 38c of the transducer element 44c and the back electrode 38d of the transducer element 44d.

Moreover, the transmitting-circuit unit 48 and the receiving-circuit unit 50 are connected by a connector 52 provided in the ultrasonic probe 40 to a control circuit 62, a signal-processing circuit 64 and a display 66, all incorporated in the ultrasonic diagnostic apparatus 60.

The control circuit 62 provided in the ultrasonic diagnostic apparatus 60 controls the ultrasonic probe 40. The signal-processing circuit 64 receives, via the connector 52, a signal generated by a transducer 44 of the probe 40. The circuit 64 performs analog-to-digital conversion on the signal, generating a digital signal. The digital signal is supplied to the display 66 that is, for example, a CRT monitor. The display 66 therefore displays a tomogram after an envelope, for example, has been detected.

During the signal transmission, the receiving circuits $50_1$ and $50_2$ remain short-circuited. The return currents supplied from the two transmitting circuit $48_1$ and $48_2$ therefore flow through the associated receiving circuits $50_1$ and $50_2$, respectively. However, the back electrodes 38 are at a potential equal to the ground potential (GND) because a potential difference scarcely develops between the receiving circuits $50_1$ and $50_2$. During the signal reception, the transmitting circuit $48_1$ and $48_2$ remain at a constant voltage. The transmitting circuit $48_1$ and $48_2$ are therefore set at a potential equal to the ground (GND) potential in terms of alternating current and are disconnected in terms of direct current due to the insulating property of the ultrasonic transducer unit. In the present embodiment, the transmitting circuit $48_1$ and $48_2$ may not be at the GND potential during the reception. Nonetheless, the transmitting circuit $48_1$ and $48_2$ receive no influence even if they remain at different potentials.

Figure 6:
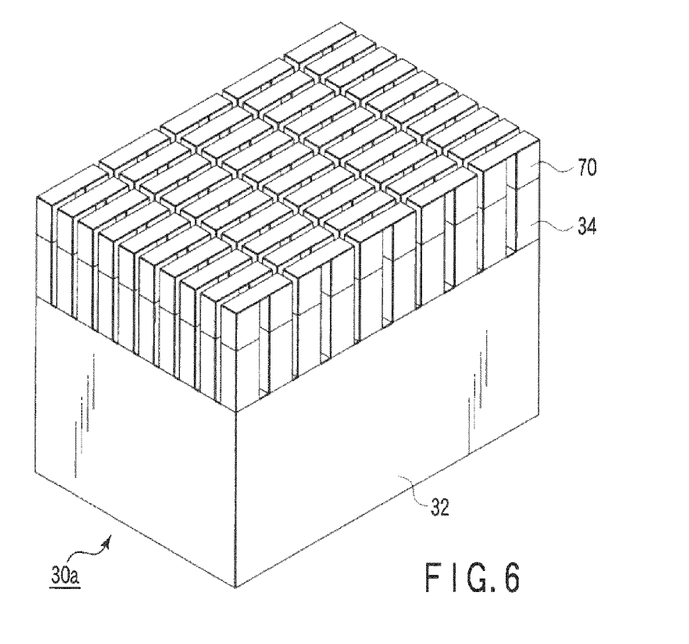
FIG. 6 is a perspective view showing a different ultrasonic transducer unit that may be incorporated in the two-dimensional array ultrasonic probe according to the first embodiment.

FIG. 6 is a perspective view showing a different ultrasonic transducer unit that may be incorporated in the two-dimensional array ultrasonic probe according to the first embodiment.

As shown in FIG. 6, the ultrasonic transducer unit 30a of the two-dimensional array ultrasonic probe comprises a backing material 32, a plurality of ultrasonic transducer elements 34, and a plurality of acoustic adjustment layers 70. The transducer elements 34 and the acoustic adjustment layers 70 are arranged on the backing material 32, in the form of a two-dimensional lattice. Electrodes are provided on the acoustic emission surfaces of the elements 34, and other electrodes are provided on the backs of the elements 34, which contact backing material 34. These electrodes are connected to transmitting circuits (not shown) and receiving circuits (not shown). The acoustic adjustment layers 70 may be of the type that has an acoustic member such as an acoustic lens or a bio-contact member.

In any other structural respect, the ultrasonic transducer unit 30a is identical to the ultrasonic transducer unit 30 (FIG. 3) of the two-dimensional array ultrasonic probe. Therefore, the components identical to those of the unit 30 are designated by the same reference numbers and will not be described in detail.

The operating principle and advantages of the ultrasonic transducer unit according to the present embodiment will be described.

Figure 7A:
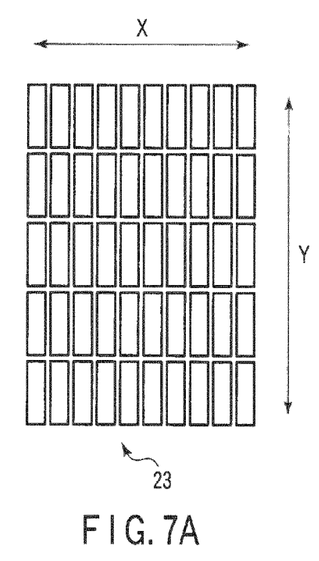
FIGS. 7A and 7B are plan views representing patterns in which the electrodes are arranged in the two-dimensional array probe according to the first embodiment, FIG. 7A showing the electrode pattern on the acoustic emission surface, and FIG. 7B showing the electrode pattern on the back.
Figure 7B:
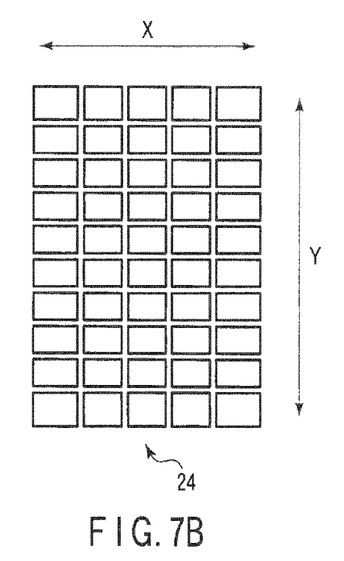

FIGS. 7A and 7B are plan views representing patterns in which the electrodes are arranged in the two-dimensional array probe according to the first embodiment, FIG. 7A showing the electrode pattern on the acoustic emission surface (i.e., transmission side), and FIG. 7B showing the electrode pattern on the back (i.e., reception side).

These electrode patterns correspond to an arrangement of transmitting elements and an arranged of receiving elements, respectively. As FIG. 4, FIG. 7A and FIG. 7B show, the acoustic-emission electrode 36 are arranged in the X-direction at the same pitch the piezoelectric element 34 are arranged, and in the Y-direction at twice the pitch the piezoelectric element 34 are arranged. The back electrodes 38 are arranged in the X-direction at twice the pitch the piezoelectric element 34 are arranged, and in the Y-direction at the same pitch as the piezoelectric element 34 are arranged. In this electrode pattern, the Y-direction pitch of transmitting elements and the X-direction pitch of receiving elements are, respectively, twice the Y- and X-direction pitches in the conventional two-dimensional array probe described above.

Figure 8A:
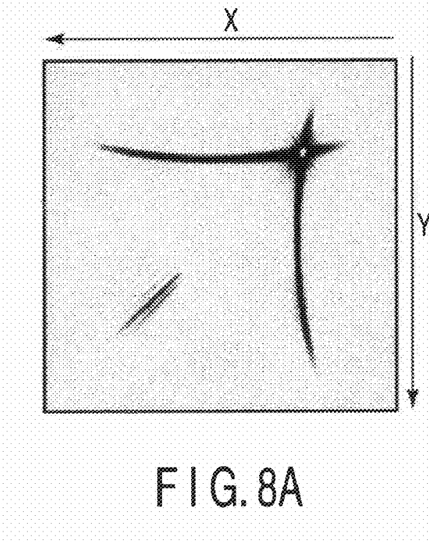
FIGS. 8A to 8C are diagrams depicting the sound fields that an ordinary two-dimensional array probe may have.
Figure 8B:
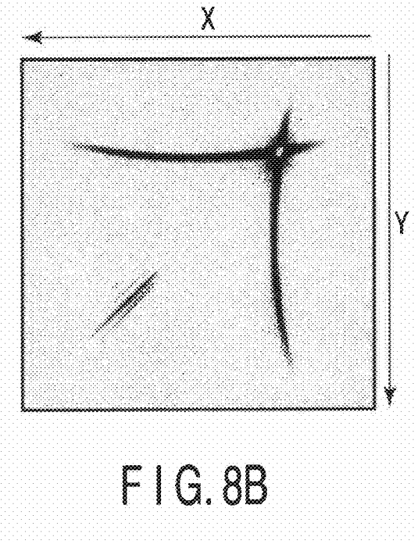
Figure 8C:
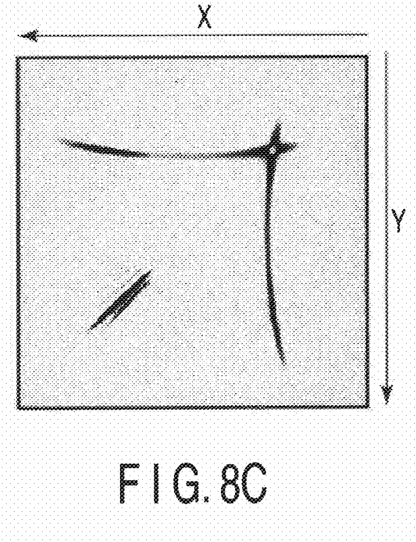

FIGS. 8A to 8C are diagrams depicting the two-dimensional directivity, i.e., sound fields, which an ordinary two-dimensional array probe has. For the sake of explanation, the X- and Y-directions are represented as lines that incline at a specific deflection angle (e.g., 40), and FIGS. 8A to 8C show all quarters of the X-Y plane each.

Each ultrasonic transducer element is connected to a transmitting circuit and a receiving circuit, independently of any adjacent element. Hence, each element has a delay time appropriate for its position. Thus, as long as the transmitting circuit and the receiving circuits have the same characteristics and the same aperture width, the transmitting sound field shown in FIG. 8A and the receiving sound field shown in FIG. 8B are identical to each other. FIG. 8C shows a transmitting/receiving sound field that is a product of the transmitting sound field (FIG. 8A) and the receiving sound field (8B), which is given by a complex number. As seen from FIGS. 8A to 8C, grating lobes develop, extending in the X-direction, Y-direction and an oblique direction, respectively. The oblique direction pertains to a structural period.

Figure 9A:
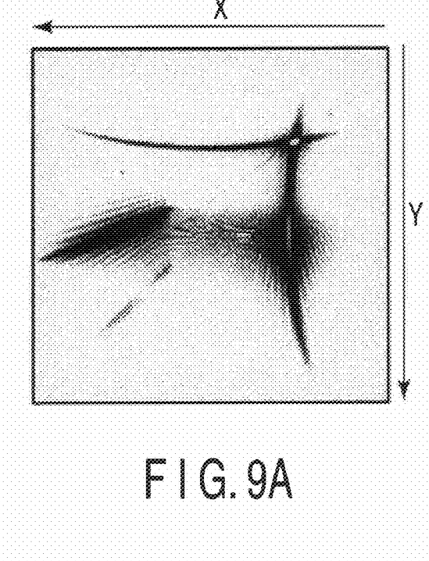
FIGS. 9A to 9C are diagrams depicting the sound fields that may be generated if two transmitting circuits are connected in parallel in the Y-direction and two receiving circuits are connected in parallel in the X-direction.
Figure 9B:
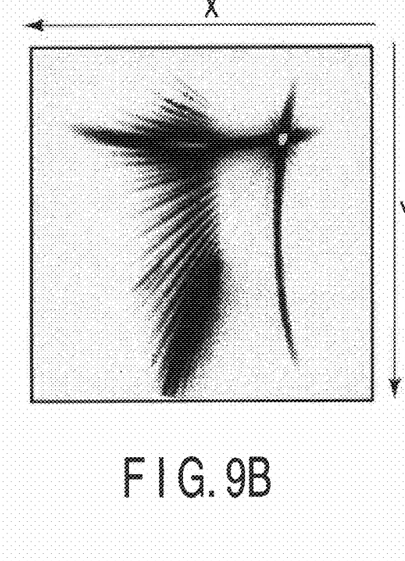
Figure 9C:
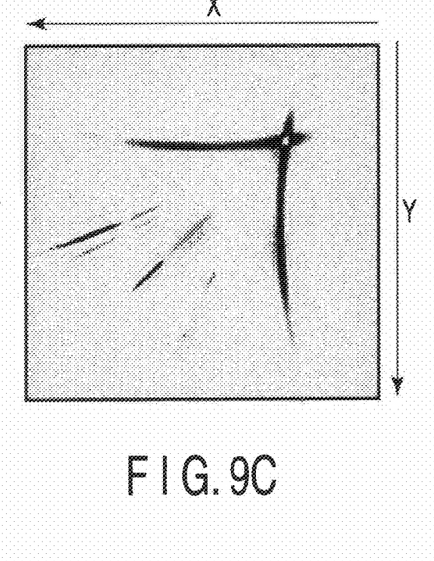

FIGS. 9A to 9C depict sound fields that are generated if two transmitting circuits for two elements are connected in parallel in the Y-direction as shown in FIG. 7A and two receiving circuits for two elements are connected in parallel in the X-direction as shown in FIG. 7B. More precisely, FIG. 9A shows a transmitting sound field, FIG. 9B shows a receiving sound field, and FIG. 9C shows a product of the sound field (FIG. 9A) and the receiving sound field (9B), which is given by a complex number.

As shown in FIG. 9A, the grating lobe is intense in the Y-direction because the transmitting elements are arranged in the Y-direction at a pitch twice as long. The grating lobe is intense also in a direction which is a little oblique to the X-direction, unlike the grating lobe shown in FIG. 8A. As shown in FIG. 9B, the grating lobe is intense in the X-direction because the transmitting elements are arranged in the X-direction at a pitch twice as great. This grating lobe is intense also in a direction a little oblique to the Y-direction, unlike the grating lobe shown in FIG. 8B.

The grating lobe shown in FIG. 9A is intense in one direction, whereas the grating lobe shown in FIG. 9B is intense in another different direction. Hence, these grating lobes cancel out each other. This is why no grating lobes develop in the transmitting/receiving sound field of FIG. 9C.

Comparison of FIGS. 8C and 9C reveals that the grating lobe shown in FIG. 9C is a little more intense than the grating lobe shown in FIG. 8C. It should be note that the transmitting circuits and the receiving circuits are used in half the number they are provided in the conventional two-dimensional array probe since the electrodes for adjacent elements are short-circuited in both the transmitting circuits and the receiving circuits.

In view of this, consider a two-dimensional array transducer unit that satisfies the following equations:

$Nx'=1.4Nx$ $Ny'=1.4Ny$ $Px'=Px/1.4$ $Py'=Py/1.4$ where $Nx'$ is the pitch at which transducer elements are arranged in the X-direction, $Ny'$ is the pitch at which the transducer elements are arranged in the Y-direction, $Nx$ is the number of elements forming each row extending in the X-direction, and $Ny$ is the number of elements forming each column extending in the X-direction.

In this two-dimensional array transducer unit, as described above, two adjacent elements arranged in the Y-direction is short-circuit during the signal transmission, and two adjacent elements arranged in the X-direction are short-circuit during the signal reception. Using this transducer unit, the two-dimensional array probe according to the present embodiment has the same aperture width and almost the same number of transmitting circuits and receiving circuits as the conventional two-dimensional array probe.

Figure 10A:
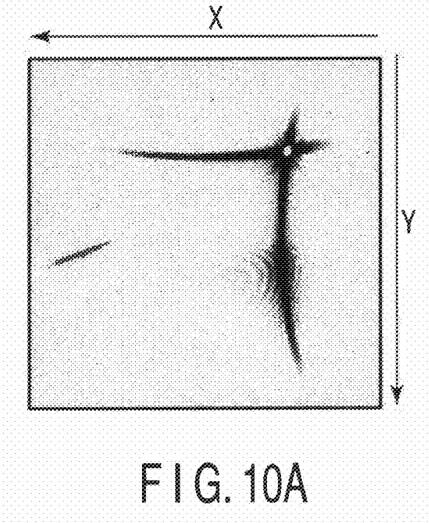
FIGS. 10A to 10C are diagrams depicting the sound fields that the two-dimensional array probe according to the first embodiment of this invention may have.
Figure 10B:
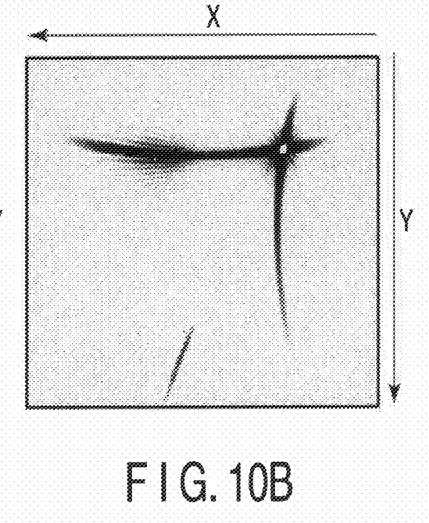
Figure 10C:
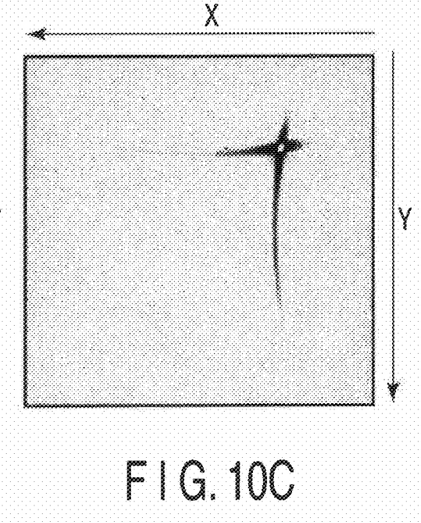

FIGS. 10A to 10C are diagrams depicting the sound fields that the two-dimensional array probe according to the first embodiment of this invention may have. Since the elements are arranged at short pitches, the grating lobes shown in FIGS. 10A and 10B have low level. In the sound field of FIG. 10C, no grating lobes are observed at all in this embodiment, unlike in the sound field of FIG. 9C.

That is, if transmitting circuits and receiving circuits are used in the same number and the aperture is as large as in the conventional two-dimensional array probe, it is possible to prevent grating lobes from developing. This means that the two-dimensional array probe can have a larger aperture if grating lobes are allowed to develop at the same level as in the conventional two-dimensional array probe. The probe can therefore be improved in sensitivity and resolution.

The present embodiment is also advantageous in that the element pitch is about 0.7 times the element pitch of the conventional probe, thus improving the shape ratio of the piezoelectric elements, so long as the probe has the same aperture.

Generally, the elements are arranged in less number in the X- or Y-direction in a two-dimensional array than in a one-dimensional array. Therefore, each element is broader than in the one-dimensional array. The two-dimensional array is easily influenced by lateral vibration, i.e., unnecessary vibration. In order to make the two-dimensional array less influenced, the technical called sub-dicing may be employed, diving each element along a vertical or horizontal line. If the element is divided into two segments, however, each segment, i.e., one piezoelectric element will be too narrow to be mechanically strong enough.

In the present embodiment, the element pitch is about 70% of the pitch applied to the conventional two-dimensional array probe. Hence, the elements can have not only a shape ratio that suppresses unnecessary vibration, but also a width that ensures sufficient strength.

Second Embodiment

A second embodiment of the present invention will be described.

Figure 11A:
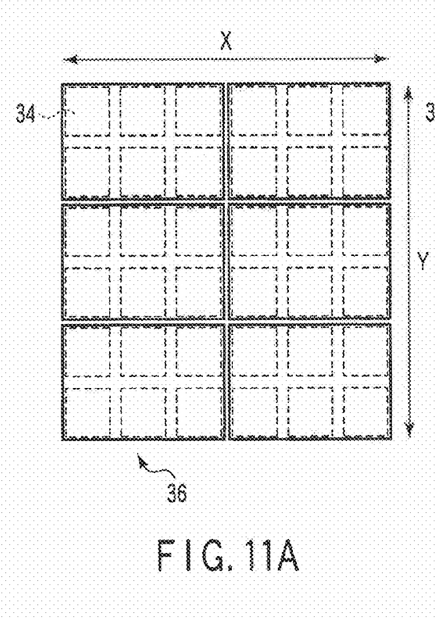
FIGS. 11A and 11B are plan views representing patterns in which the electrodes are arranged in a two-dimensional array probe according to a second embodiment, FIG. 11A showing the electrode pattern on the acoustic emission surface, and FIG. 11B showing the electrode pattern on the back.
Figure 11B:
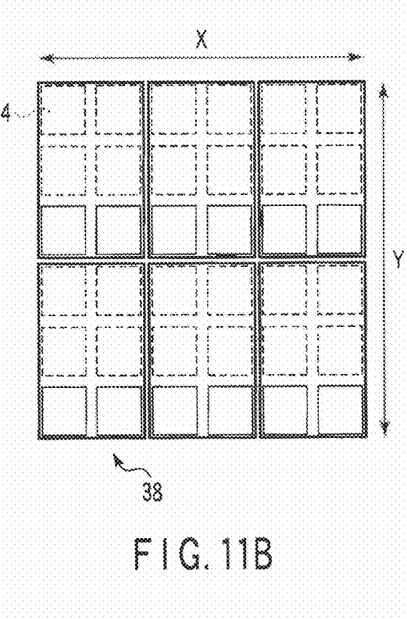

FIGS. 11A and 11B are plan views representing patterns in which the electrodes are arranged in a two-dimensional array probe according to a second embodiment. FIG. 11A shows the electrode pattern on the acoustic emission surface. FIG. 11B shows the electrode pattern on the back.

In the second embodiment, the acoustic-emission electrode 36 are arranged in the X-direction, forming two columns, and in the Y-direction, forming three rows. Conversely, the back electrodes 38 arranged in the X-direction, forming three columns, and in the Y-direction, forming two rows. Each acoustic-emission electrode 36 connects, by short-circuiting, six piezoelectric elements 34. Each back electrode 38 connects, by short-circuiting, six piezoelectric elements 34. Thus, the piezoelectric elements 34, acoustic-emission electrode 36 and back electrodes 38 constitute a transducer unit. This configuration of the transducer unit is desirable in the case where the piezoelectric elements must be arrange at shorter pitches than in the first embodiment, because of their shape ratio.

In the first embodiment, the pitches at which the elements are arranged in the X- and Y-directions during the signal transmission greatly differs from the pitches at which the elements are arranged in the X- and Y-directions during the signal reception, and the elements may be unbalanced in terms of directivity (element factor). In the second embodiment, the pitch at which the elements are arranged in the X-direction is similar to the pitch at which they are arranged in the Y-direction. Hence, elements are scarcely unbalanced in terms of directivity. The direction in which the grating lobes extend during the signal transmission is indeed similar to the direction in which they extend during the signal reception. Nevertheless, the array has directivity high enough to suppress grating lobes during both the signal transmission and the signal reception.

In the embodiment previously described, the elements are arranged in the form of a 1×2 lattice or a 2×3 lattice. The elements can be arranged in any other pattern and connected by short-circuiting. That is, this invention is characterized in that the electrodes are arranged in a pattern on the acoustic emission surface and in another pattern on the back. Therefore, the grating lobes extend in one direction during the signal transmission and in another direction during the signal reception. Any transducer unit that has such a short-circuit pattern and such a circuit configuration falls within the scope of the present invention.

Third Embodiment

A third embodiment of the present invention will be described.

In the first and second embodiments described above, the acoustic-emission electrode are arrange, forming a lattice, and the back electrodes are arranged, forming a lattice, and each acoustic-emission electrode intersects at right angles with one back electrode. The electrodes may be arranged in any other pattern. In the third embodiment, the electrodes are arranged in a zigzag pattern or in a honeycomb pattern.

Figure 12A:
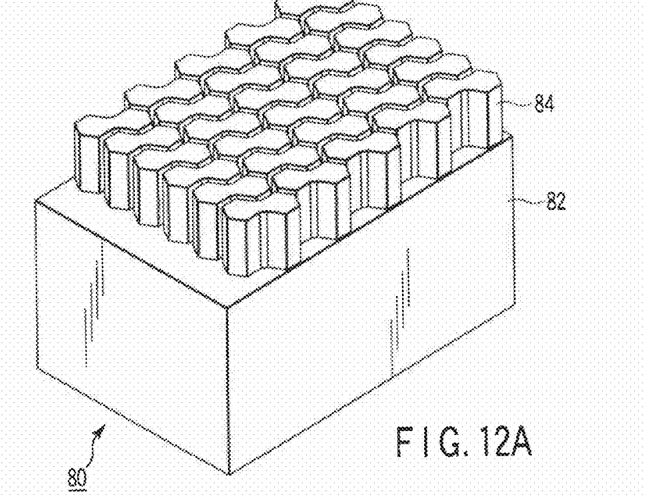
FIGS. 12A to 12C show the arrangement of the transducer elements of a two-dimensional array ultrasonic probe according to a third embodiment of this invention, FIG. 12A being a perspective view of the probe, FIG. 12B being a perspective view showing the electrode pattern of the probe, and FIG. 12C being a plan view showing the electrode pattern of the probe.
Figure 12B:
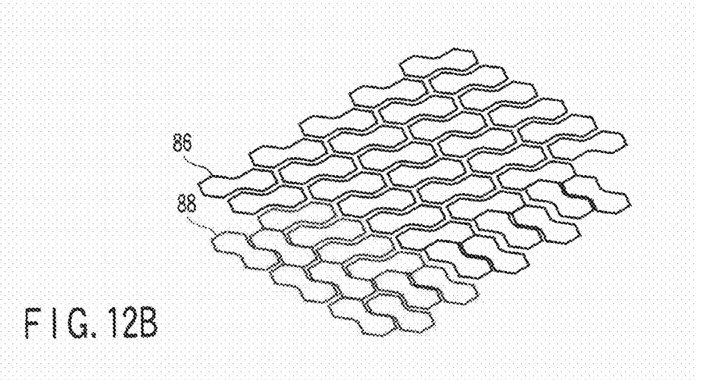
Figure 12C:
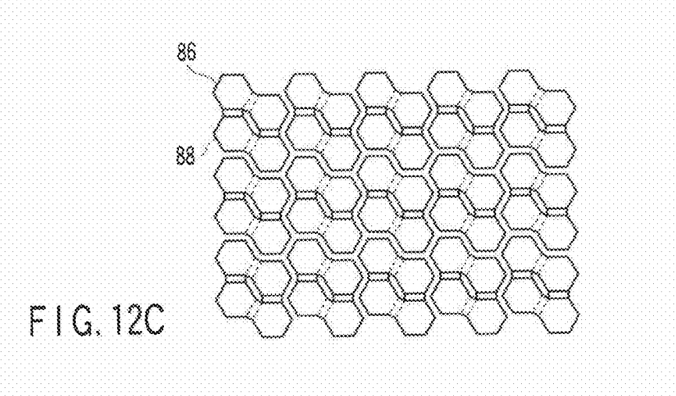

FIGS. 12A to 12C show the arrangement of the transducer elements of a two-dimensional array ultrasonic probe according to the third embodiment of this invention. FIG. 12A is a perspective view of the probe. FIG. 12B is a perspective view showing the electrode pattern of the probe. FIG. 12C is a plan view showing the electrode pattern of the probe.

As FIG. 12A shows, the transducer unit 80 of the two-dimensional array ultrasonic probe comprises a backing material 82 and a plurality of ultrasonic transducer (piezoelectric) elements 84. The ultrasonic transducer elements 84 are shaped like a hexagonal prism and are arranged on the backing material 32, in a honeycomb pattern. Electrodes are provided on the acoustic emission surfaces of the elements 34, and other electrodes are provided on the backs of the elements 84, which contact backing material 82. These electrodes are connected to transmitting circuits (not shown) and receiving circuits (not shown). Further, an acoustic member, such as an acoustic adjustment layer, an acoustic lens or a bio-contact member, is arranged on the acoustic emission surface of each transducer element 84.

FIGS. 12B and 12C show the arrangement of the transducer elements 84 shown in FIG. 12A. More precisely, FIG. 12B is a perspective view of the electrodes, and FIG. 12C is a plan view of the electrodes. FIGS. 12B and 12C show only the acoustic-emission electrode 86 and back electrodes 88. In this embodiment, any two adjacent piezoelectric elements 84 arranged in a first direction are short-circuited by one acoustic-emission electrode 86 provided on their acoustic emission surfaces, and any two adjacent piezoelectric elements 34 arranged in a second direction intersecting at right angles with the first direction are short-circuited by one electrode 38 provided on their backs.

Transmitting circuits (not shown) are connected to the acoustic-emission electrodes 86 and receiving circuits (not shown) are connected to the back electrodes 88, by a signal-line board, such as a flexible printed-circuit (FPC) board. As a result, the two-dimensional array ultrasonic transducer unit 80 has such a circuit configuration as shown in FIG. 5.

Since the transducer elements are shaped like a hexagonal prism and are arranged in a honeycomb pattern, this embodiment can attain the same advantages as the first and second embodiments and can have higher area-use efficiency.

In the third embodiment, the transducer elements are shaped like a hexagonal prism. Instead, the transducer elements may be membrane-shaped ones such as capacitive micro-machined ultrasonic transducers (CMUT). If this is the case, disc-shaped transducer elements are arranged on a flat plate.

If the transducer unit comprises membrane-shaped transducer elements, represented by CMUTs, it will achieve the same advantages.

Fourth Embodiment

A fourth embodiment of the invention will be described.

The first to third embodiments, which have been described, are two-dimensional array ultrasonic probes. Nonetheless, the present invention can be applied to one-dimensional array ultrasonic probes, too.

Figure 13:
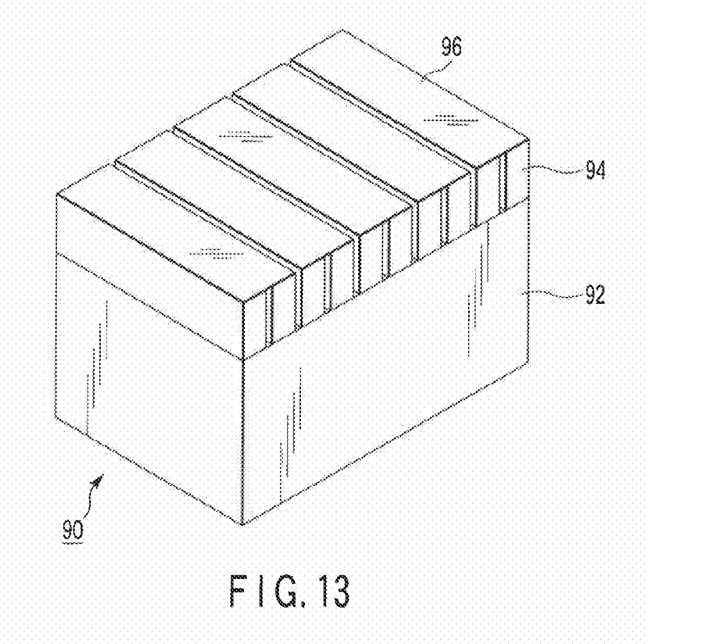
FIG. 13 is a perspective view showing the configuration of the transducer unit of a one-dimensional array ultrasonic probe according to a fourth embodiment of this invention.

FIG. 13 is a perspective view showing the configuration of the transducer unit of a one-dimensional array ultrasonic probe according to a fourth embodiment of this invention.

As shown in FIG. 13, this transducer unit 90 comprises a backing material 92 and a plurality of ultrasonic transducer elements 94. The transducer (piezoelectric) element 94 are shaped like a rectangular bars and arranged on the backing material 92, in one direction. A plurality of electrodes 96 are formed on the acoustic emission surfaces of the transducer (piezoelectric) element 94, respectively. A plurality of electrodes are formed on the backs of the elements 94, which contact the backing material 92. The acoustic-emission electrodes 96 are connected to transmitting circuits (not shown), and the back electrodes are connected to receiving circuits (not shown). Further, an acoustic member, such as an acoustic adjustment layer, an acoustic lens or a bio-contact member, is arranged on the acoustic emission surface of each transducer element 84.

Figure 14:
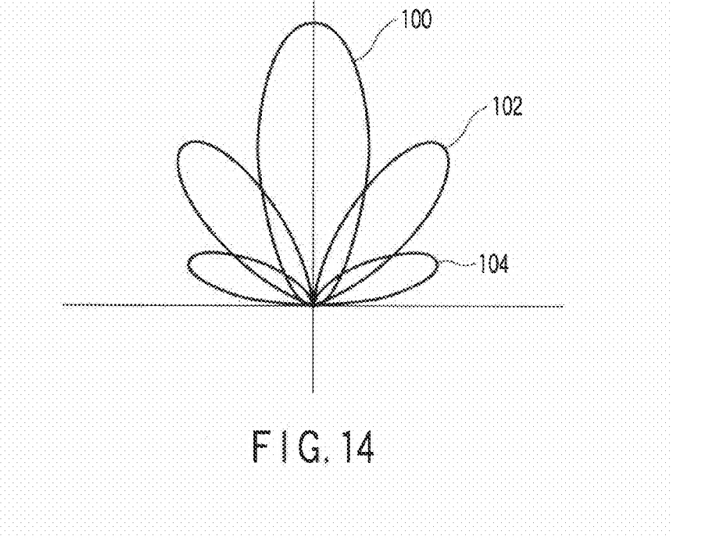
FIG. 14 is a diagram depicting a sound field having a sound field that the one-dimensional array ultrasonic probe according to the fourth embodiment may have.

FIG. 14 is a diagram depicting a sound field having a sound field that the one-dimensional array ultrasonic probe according to the fourth embodiment may have.

In the transducer unit 90 according to the fourth embodiment, each back electrode (not shown) is short-circuited to one piezoelectric element, and each acoustic-emission electrode 96 is short-circuited to two piezoelectric elements.

The transducer unit 90 thus configured emits a main beam 100 shown in FIG. 14. During the signal emission, grating lobes 102 develop. During the signal reception, grating lobes 104 develop. The grating lobes 102 developing during the signal transmission and the grating lobes 104 developing during the signal reception differ in the direction they extend. Therefore, they do not practically influence an image.

Thus, the fourth embodiment can achieves the same advantages as the first to third embodiments. Moreover, the fourth embodiment can reduce the transmitting-circuit section and the receiving-circuit section to half the size of the conventional circuit sections.

In the embodiments described above, the transmitting circuits are connected to the acoustic-emission electrodes, and the receiving circuits are connected to the back electrodes. Instead, the transmitting circuits may be connected to the back electrodes, and the receiving circuits may be connected to the acoustic-emission electrodes. In this case, too, the advantages described above can be attained.

In the embodiments described above, each of the ultrasonic transducer elements (piezoelectric elements) is short-circuited to an acoustic-emission electrode and to a back electrode. This invention is not limited to this configuration. For example, the ultrasonic transducer elements may be short-circuited to a circuit board comprising the transmitting circuits and to a circuit board comprising the receiving circuits.

In the embodiments described above, the transmitting circuits and the receiving circuits are provided in the probe head. Instead, they may be provided in the connector unit or in the main unit of the diagnostic apparatus. In this case, too, the advantages described above can be achieved.

Several embodiments of the present invention have been described. Nonetheless, various changes and modifications can be made, without departing from the scope and spirit of the present invention.

Further, the embodiments described above include various phases of the invention. The components disclosed herein may be combined in various ways to make various inventions. Even if some components of any embodiment described above are not used, it is possible to solve the problems specified in the "SUMMARY OF THE INVENTION." Any configuration not using some components can be considered as the invention so long as it achieves at least one of the advantages that will be stated in the following paragraph.

The present invention can provide a two-dimensional array ultrasonic probe that has as small a transmitting-circuit section and a receiving-circuit section as possible and yet has a large aperture and high sensitivity, not influenced by grating lobes, and also an ultrasonic diagnostic system that has such a two-dimensional array ultrasonic probe.

Since the piezoelectric elements can easily be arranged at such an optimal pitch that they may have a desired shape ratio. The elements can therefore be prevented from degrading in their ultrasonic transmitting-receiving characteristic.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe comprising:
a plurality of ultrasonic transducer elements, each of which has a first electrode and a second electrode provided on an acoustic-emission surface and a back, respectively;
transmitting circuits each of which is connected to one of the first and second electrodes; and
receiving circuits each of which is connected to the other of the first and second electrodes,
wherein at least two of adjacent ultrasonic transducer elements are short-circuited to each other by the first and second electrodes, and the first and second electrodes achieve short-circuiting in different patterns.

2. The ultrasonic probe according to claim 1, wherein the ultrasonic transducer elements are arranged in a direction intersecting at right angles with the acoustic-emission surface, and form a one-dimensional array.

3. The ultrasonic probe according to claim 1, wherein the number of transducer elements short-circuited by the first electrode is different from the number of transducer elements short-circuited by the second electrode.

4. The ultrasonic probe according to claim 1, wherein the adjacent transducer elements are short-circuited by the first electrode, and other adjacent transducer elements are short-circuited by the second electrode.

5. The ultrasonic probe according to claim 1, wherein the number of transducer elements short-circuited by one of the first and second electrodes is twice the number of transducer elements short-circuited by the other of the first and second electrodes.

6. The ultrasonic probe according to claim 1, wherein the number of transducer elements short-circuited by one of the first and second electrodes is 1.5 times the number of transducer elements short-circuited by the other of the first and second electrodes.

7. The ultrasonic probe according to claim 1, wherein two adjacent transducer elements are short-circuited by the first electrode and the second electrode.

8. The ultrasonic probe according to claim 1, wherein the ultrasonic transducer elements are arranged in a plane intersecting at right angles with an acoustic-emission direction, and form a two-dimensional array.

9. The ultrasonic probe according to claim 1, wherein the ultrasonic transducer elements are arranged in a honeycomb pattern, in a plane intersecting at right angles with an acoustic-emission direction, and form a two-dimensional array.

10. The ultrasonic probe according to claim 1, wherein the ultrasonic transducer elements are arranged in two directions intersecting at right angles with each other and with an acoustic-emission direction, and form a two-dimensional array shaped like a lattice.

11. The ultrasonic probe according to claim 10, wherein the short-circuiting by the first electrode and the short-circuiting by the second electrode are achieved, each by short-circuiting adjacent ultrasonic transducer elements, and the direction in which the ultrasonic transducer elements are short-circuited by the first electrode and the direction in which the ultrasonic transducer elements are short-circuited by the second electrode intersect at right angles with each other.

12. The ultrasonic probe according to claim 10, wherein the short-circuiting by the first electrode and the short-circuiting by the second electrode are achieved, each by short-circuiting adjacent two ultrasonic transducer elements, and the direction in which the ultrasonic transducer elements are short-circuited by the first electrode and the direction in which the ultrasonic transducer elements are short-circuited by the second electrode intersect at right angles with each other.

13. The ultrasonic probe according to claim 10, wherein the short-circuiting by the first electrode is achieved by shorting-circuiting two ultrasonic transducer elements arranged in a first direction and three ultrasonic transducer elements arranged in a second direction intersecting at right angles with the first direction, and the short-circuiting by the second electrode is achieved by shorting-circuiting three ultrasonic transducer elements arranged in the first direction and two ultrasonic transducer elements arranged in the second direction.

14. The ultrasonic probe according to claim 1, wherein the short-circuiting by the first and second electrodes is achieved by using conductor patterns provided on a printed circuit board that is connected directly or via an adjustment layer to the ultrasonic transducer elements.

15. The ultrasonic probe according to claim 14, wherein the printed circuit board is a flexible printed circuit board which is composed of a base made of polyimide film and a conductor pattern made of copper foil and formed on the base.

16. The ultrasonic probe according to any one of claims 1, 2, 8, 9 and 14, wherein transmitting circuits are connected, each to one of the first and second electrodes, and receiving circuits are connected, each to the other of the first and second electrodes.

17. The ultrasonic probe according to claim 1, wherein the short-circuiting to the first electrode and the short-circuiting by the second electrode are achieved, each by a transmitting/receiving circuit board connected to the ultrasonic transducer elements.

18. An ultrasonic diagnostic system having an ultrasonic probe designed to apply and receive ultrasonic waves to and from a subject, thereby to acquire information about tissues existing in the subject,
wherein the ultrasonic probe comprises a plurality of ultrasonic transducer elements, each of which has a first electrode and a second electrode provided on an acoustic-emission surface and a back, respectively, transmitting circuits each of which is connected to one of the first and second electrodes, and receiving circuits each of which is connected to the other of the first and second electrodes; and the first and second electrodes short-circuit at least two of at least two adjacent ultrasonic transducer elements, respectively in different patterns.

19. The ultrasonic diagnostic system according to claim 18, wherein the ultrasonic transducer elements are arranged in a direction intersecting at right angles with an acoustic-emission surface, and form a one-dimensional array.

20. The ultrasonic diagnostic system according to claim 18, wherein the ultrasonic transducer elements are arranged in a honeycomb pattern, in a plane intersecting at right angles with an acoustic-emission direction, and form a two-dimensional array.

21. The ultrasonic diagnostic system according to claim 18, wherein the ultrasonic transducer elements are arranged in two directions intersecting at right angles with each other and with an acoustic-emission direction, and form a two-dimensional array shaped like a lattice.

* * * * *